(12) United States Patent
Tada et al.

(10) Patent No.: US 6,613,398 B1
(45) Date of Patent: Sep. 2, 2003

(54) METHOD FOR IMPROVING SOLUBILITY OF PROTEIN

(75) Inventors: Mikiro Tada, 1-3-1-102, Tushimanaka, Okayama-shi, Okayama 700-0082 (JP); Kazushi Sakaue, Osaka (JP); Toru Hayashi, Ushiku (JP); Setsuko Suzuki, Tsukuba (JP)

(73) Assignees: Director of National Food Research, Institute, Ministry of Agriculture, Forestry and Fisheries, Ibaraki (JP); Mikiro Tada, Okayama (JP); San-Ei Gen F.F.I., Inc., Osaka (JP)

( * ) Notice: Subject to any disclaimer, the term of this patent is extended or adjusted under 35 U.S.C. 154(b) by 0 days.

(21) Appl. No.: 09/857,781

(22) PCT Filed: Dec. 9, 1999

(86) PCT No.: PCT/JP99/06930

§ 371 (c)(1),
(2), (4) Date: Aug. 13, 2001

(87) PCT Pub. No.: WO00/34311

PCT Pub. Date: Jun. 15, 2000

(30) Foreign Application Priority Data

Dec. 10, 1998 (JP) .......................................... 10-351003

(51) Int. Cl.$^7$ ................................................. B05D 3/00
(52) U.S. Cl. ........................ 427/551; 427/144; 427/180; 427/196; 427/595
(58) Field of Search .............................. 427/551, 595, 427/180, 144, 196

(56) References Cited

U.S. PATENT DOCUMENTS 6,013,856 A * 1/2000 Tucker et al. ................. 623/16

FOREIGN PATENT DOCUMENTS

JP  A7016085  1/1995
JP  7-016085 A  1/1995

OTHER PUBLICATIONS

Biglow, C., J. Theoret. Biol., 16, 187–211 (1967) (No month avail.).
Ribadeau–Dumas, B. et al., Eur. J. Biochem. 26, 328–337 (1972) (No month avail.).
J.C. Chefte et al., Proteines Alimentaires (1998) (No month avail.).
H. Van del Wel, Eur. J. Biochem., 31, pp. 221–225 (1972) (No month avail.).
Kenya Kamei, Protein Analysis by Windows, Kyoritsu Shuppan (1997) (No month avail.).
Atsuji Watanabe et al., Soybean Food, pp. 18, Korin (1971) (No month avail.).
Yusuke Asano et al., Egg, pp. 64, Korin (1985) (No month avail.).
S. Uenogawa, A Handbook of Engineering Functional Food Protein, pp. 17, Science Forum (1991) (No month avail.).
K. Sakaue et al., Functional Changes of Taumatin by Electron Beam Irradiation, Shokuhin Shosha, 32:1/2, pp. 13–19 (1997) (No month avail.).
Sakaue et al., Shokuhin Shosha, vol. 32, Nos. 1/2, pp. 13–19 (1997) (No month avail).
Saito et al., Shokuhin Shosha, vol. 22, No. 2, pp. 26–30 (1987) (No month avail).

* cited by examiner

*Primary Examiner*—Bernard Pianalto
(74) *Attorney, Agent, or Firm*—Birch, Stewart, Kolasch and Birch, LLP

(57) ABSTRACT

According to the present invention, provided is a method for improving solubility of a protein in water by irradiating the protein with an electron beam. According to the method, the solubility of the protein in water is improved without alteration and decomposition of the protein and an associated body which is not generated in an ordinary state is formed, so that protein which is stable even in an aqueous solution can be obtained.

9 Claims, 2 Drawing Sheets

METHOD FOR IMPROVING SOLUBILITY OF PROTEIN

This application is the national phase under 35 U.S.C. §371 of PCT International Application No. PCT/JP99/06930 which has an International filing date of Dec. 9, 1999, which designated the United States of America.

TECHNICAL FIELD

The present invention relates to a method for improving solubility of a protein by irradiating the protein with an electron beam, the protein treated by said method and a product containing the protein treated by said method.

BACKGROUND ART

In general, proteins used for food and industry include water-soluble proteins and water-dispersible proteins. For utilization of the proteins, there has been demanded improvement of nutrition and functional properties such as capacities of holding water, gelating, adding viscosity, emulsifying, bubbling, adding body, solidifying, adding taste, flavoring, or adding preservability, sweetening, as well as enzyme activation.

Among conventionally used proteins, few kinds of proteins are water-soluble. A common method for dissolving the protein in water is to change acidity or basicity (pH) of a solution by using an alkali or an acid.

For dissolving a water-dispersible protein in water, the following means other than changing pH are usually employed.

As to muscle proteins such as actin and myosin contained in animal meat and fish meat, it is known that their solubility in water is improved by a salt-solubilization using sodium chloride, or solubilization with a salt having chelating ability by adding a sodium citrate or a polyphosphate such as tripolyphosphate. The process utilizing sodium chloride is applied not only to animal proteins but also to plant proteins such as wheat proteins. Further, as to milk-derived proteins such as acid casein, improvement of water solubility is realized by salification through addition of sodium hydroxide, potassium hydroxide or calcium hydroxide. Moreover, it is also known as a method for improving the solubility to decompose proteins to lower molecular proteins by using acids such as hydrochloric acid or enzymes such as protease.

As described above, functional properties of the protein such as capacities of emulsifying, thickening, holding water and gelating are extracted by improving the solubility. In order to make the best use of the functional properties, the solubility of the protein in water must be improved. However, the properties are not fully exhibited by the known methods.

Thus, it has been demanded an easily operatable and industrially inexpensive method capable of large-scale treatment for improving the water solubility of the protein without alteration and decomposition of the protein.

DISCLOSURE OF INVENTION

As a result of eager researches to solve the above-mentioned problems, the inventors of the present invention have found that irradiation of a protein with an electron beam improves the water solubility.

According to the present invention, provided is a method for improving solubility of a protein in water by irradiating the protein with an electron beam, the protein treated by said method, and a product containing the protein treated by said method.

BEST MODE FOR CARRYING OUT THE INVENTION

Figure 1:
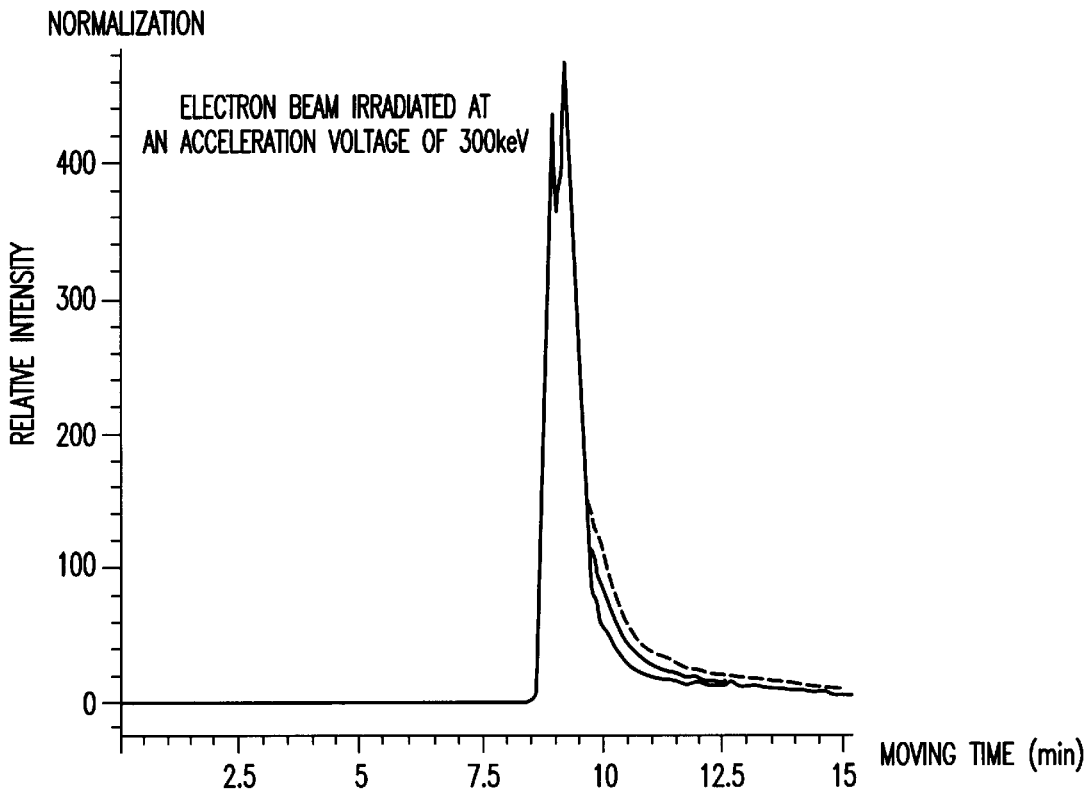
FIG. 1 is a graph illustrating changes in surface charge of thaumatin observed by capillary electrophoresis at an acceleration voltage of 300 keV. A solid line means unirradiated thaumatin, a broken line means thaumatin irradiated at an absorbed dose of 5 kGy and a dotted line means thaumatin irradiated at an absorbed dose of 25 kGy.

The proteins to be treated in the present invention are not particularly limited. However, the inventors have found that the invention is preferably applied to proteins having the degree of hydrophobicity per amino acid residue constituting the protein (hydrophobicity×protein composition (residues, molar numbers))/total number of residues [see Biglow, C., J. Theoret. Biol., 16, 187–211 (1967); Ribadeau-Dumas, B. et al., Eur. J. Biochem. 26, 328–337 (1972)] of 0.0222 or more.

Thaumatin, a sweet protein, is extracted from an aril of fruit of Thaumatococcus daneillii Benth and has 209 amino acid residues, molecular weight of 22209 daltons and 8 disulfide linkages, exhibiting an isoelectric point of 11 or more and sweetness of 3500 times greater than sugar. This is used as a food additive and has purity as high as about 99%. Also, thaumatin possesses the property that at 25° C., water does not act as a rich solvent but a poor solvent, so that an interaction with water becomes insusceptible. Preferably, the proteins used in the present invention are those having the degree of hydrophobicity of 0.0222 or more, with respect to thaumatin as an index. Accordingly, examples of the proteins applicable to the present invention include proteins shown in the following Table 1 [see Biglow, C., the aforesaid document; Ribadeau-Dumas, B. et al., the aforesaid document; J. C. Chefte et al., Proteines Alimentaires (1998); Van del Wel, H. et al., Eur. J. Biochem., 31, pp. 221–225 (1972); Kenya Kamei, Protein Analysis by Windows, Kyoritsu Shuppan (1997), Atsuji Watanabe et al., Soybean Food, pp. 18, Korin (1971); Yusuke Asano et al., Egg, pp. 64, Korin (1985); Shuichi Uenogawa, A Handbook of Engineering Functional Food Protein, pp. 17, Science Forum (1991)], plasma protein, soybean protein, soybean 11S globulin, soybean 7S globulin, as well as keratin contained in hair and nails.

TABLE 1

| Kind of Protein | Hydrophobicity | Degree of hydrophobicity |
| --- | --- | --- |
| Thaumatin | 4.60 | 0.02220 |
| Ovomucoid | 4.42 | 0.02248 |
| Papaya papain | 4.94 | 0.02332 |
| Corn zein | 5.43 | 0.02504 |
| Alpha s1 casein | 5.29 | 0.02650 |
| Sweet milaclin | 5.21 | 0.02720 |
| Beta casein | 5.84 | 0.02790 |

TABLE 1-continued

| Kind of Protein | Hydrophobicity | Degree of hydrophobicity |
|---|---|---|
| Bovine brain calmodulin | 4.31 | 0.02910 |
| Wheat globulin | 4.28 | 0.03120 |
| Kappa casein | 5.36 | 0.03170 |
| Human placenta HMG-1 (Y) | 3.78 | 0.03433 |
| Human blood hemoglobin b | 5.07 | 0.03475 |
| Human blood hemoglobin a | 4.96 | 0.03521 |
| Avidin (egg) | 4.62 | 0.03580 |
| Wheat glutenin | 5.01 | 0.03650 |
| Sweet curculin | 4.31 | 0.03780 |
| Wheat gluten | 5.30 | 0.03860 |
| Wheat gliadin | 5.44 | 0.03970 |
| Egg lysozyme | 4.79 | 0.04027 |
| Ficin inhibitor | 4.80 | 0.04160 |
| Sweet mabinilin | 4.83 | 0.04600 |
| Human cytochrome c | 5.15 | 0.04950 |
| Ovomucin | 5.13 | 0.06610 |
| Ovomacroprotein | 5.50 | 0.08000 |
| Bovine sperm protamin | 3.91 | 0.08499 |

Further, also listed are monellin, milt protein, poly-lysine, taurine, betaine, mutasteine, ice nucleation protein, lactoferrin, sepia, gelatin, rennet casein, amylase, transferase, pepsin and the like. Among them, thaumatin, α-casein and plasma protein are preferable.

The proteins applicable to the present invention may preferably contain the above-mentioned protein of 70 wt %, preferably 80 wt %, more preferably 90 wt % or more. Common protein compounding products, protein mixture formulation and the like may also be applicable.

The method of the present invention is characterized by irradiating the protein with an electron beam. In general, the electron beam is generated by an electron beam generating machine. For example, a linear electron accelerator, a Van de Graaff's electron accelerator, an area beam type or Cockcroft-Walton's electron beam generating machine and the like are usable.

For the electron beam irradiation, an acceleration voltage to be applied to the electron beam is in a range of 50 KeV to 10 MeV, preferably 50 KeV to 5 MeV, more preferably 300 KeV to 2.5 MeV. With an electron beam applied with an acceleration voltage of less than 50 KeV, expected effects can not be obtained. Use of an electron beam applied with an acceleration voltage of higher than 10 MeV to food products is prohibited.

Dose rate of the electron beam is preferably in the range of $1.0 \times 10^5$ to $1.0 \times 10^9$ Gy/hr.

It is suitable that water content of the protein applicable to the present invention is controlled to 20 wt % or less, preferably 10 wt % or less before the electron beam irradiation. The protein may be in a dried form, a dispersed form in water and the like, but preferably is in the dried form of film, plate, particles or powders in order to perform uniform irradiation of the electron beam. In the case of irradiating the protein dispersed in water with the electron beam, the protein may be solidified, if required, by spray-drying, drum-drying, or hot air-drying after the irradiation.

The electron beam irradiation can be performed in the presence of air in an open system, or in the presence of air, oxygen or nitrogen in a closed system.

The electron beam irradiation can be performed directly or indirectly to the protein. For example, in the case of the protein in the form of particles or powders, the irradiation may be performed with respect to the particles or the powders which are spread to have a thickness of 5 mm or less in a plastic vessel, preferably a polyethylene bag, having a thickness of 80 µm and capable of transmitting the electron beam.

The inventors of the present invention have found that the above-mentioned electron beam irradiation improves the solubility of the protein in water. For example, in the case of thaumatin which is generally dissolved in water at ca. 65° C., ca. 70 wt % is dissolved in water at ca. 46° C. through the electron beam irradiation. That is, dissolving temperature is reduced by about 20° C. Thus, "improvement of solubility in water" in the present invention signifies that the solubility of the protein in water of the same amount and the same temperature is increased.

Mechanism of the solubility increase of the protein through the electron beam irradiation is unknown. However, the inventors have confirmed through capillary electrophoresis that the electron beam irradiation causes a change of higher-order structure such as plus charges are exposed on the surface of thaumatin molecules. It is recognized that such charges show the same state as that where a common protein product has been converted to be water-soluble by use of a salt. Further, upon calculating a second virial coefficient representing affinity to solvents [see Eisenberg, Crothers (translated by Yoshisuke Nishimoto, Akihiro Kagemoto, Yoshihiro Baba and Eiji Tanaka), Physical Chemistry for Life Science, Baifukan, p258–259 (1979)], it has been shown that hydrophilicity increases through the irradiation. These phenomena tend to be enhanced depending on the absorbed dose of the irradiated electron beam. Therefore, it is considered that the solubility of the electron beam-irradiated protein in water is resulted from the above-mentioned phenomena.

Besides, it is further observed by measurement of molecular weight that the irradiated protein forms an associated body which is not generated in an ordinary state, e.g., a multimer such as a pentamer or a hexamer, in an aqueous solution. The formation of the associated body limits a speed of decomposition by enzymes as seen in common proteins, which indicates a possibility that high stability is maintained.

The electron beam can be used with less industrial costs and an irradiation technique therefor has already been established, so that a large amount of protein can be treated by an easy operation. Further, through a treatment according to the method of the present invention, inherent functions of the protein are not spoiled, so that the protein can be applied to various fields.

For example, the protein can be used in livestock products (ham, sausage, salami, sweet-and-sour pork, roast pork, broiled pork innards, meatball, corned beef, liver paste, hamburger steak), marine products (Kamaboko, Hanpen, fish paste, delicacy Kamaboko, fried Kamaboko, ingredients of Oden, oiled tuna, sardine or.mackerel preserved in miso, shellfish products, shrimp stewed in cream), agricultural products (deli, chop suey, salad, packed lunch, Sukiyaki, fried Tofu with hot meat sauce, stew, curry, meat sauce, soup), dairy products (coffee cream, condensed milk, soya milk, cheese, yogurt, various kinds of modified dairy products), egg products (mayonnaise, omelet, Dashimaki omelet), rice products (sushi, eel rice, pilaf, crab rice, fried rice), desserts (pudding, jerry, flan, sweet red-bean soup), frozen sweets (ice cream, shaved ice, sherbet, chopped ice) and frozen products (frozen foods), pickles (Fukujin-zuke, miso pickles, soy sauce pickles, mustard pickles, sake-lees pickles) fruit products (grapes preserved in syrup, orange juice, clear apple juice, tomato juice, tomato ketchup, tomato sauce, apricot jam, jelly, preserves, candied chestnuts), beverages (coffee, coffee-flavored milk, tea, carbonated drink, cola, soft drink, nectar, green tea), alcoholic beverages (sake, sweet alcoholic drink, water-diluted alcohol drink, fruit juice-containing drink, cocktail, wine, beer), noodle products (snack noodles, Udon, Chinese noodles, Soba, noodle sauce), wheat flour products (cake, frozen cake, flour for Okonomi-Yaki, flour for Takoyaki, flour for fried chicken), soybean products, retort-packed products, aseptic-filled products and the like. Further, the protein can also be applied to various medical supplies such as toothpaste, mouth care products and mouthwash as well as cosmetics.

In particular, in the case of the livestock products such as ham and sausage to be processed by using protein powders dissolved in water, the products of good yield can be obtained by mixing an aqueous solution containing the protein powders directly irradiated with the electron beam into another solution. Further, in the case of the dairy products such as cheese and pudding, acid casein powders are irradiated with the electron beam so that a total solid of the protein contained in the cheese or gel strength of the pudding can be increased.

EXAMPLES

Hereinafter, the present invention will be detailed with reference to examples, but the invention is not limited thereto.

Example 1

Powders of thaumatin (produced by Talin Food, Lot No. J99, containing 98 wt % of protein and 5 wt % of water) were put in a polyethylene bag (140 mm height×140 mm width×0.08 mm thickness) and spread thinly to have a thickness of 5 mm. Irradiation was performed in the presence of air.

A Van de Graaff's electron accelerator (manufactured by Nisshin High Voltage Co. Ltd.) was used for the irradiation. The irradiation was performed at acceleration voltages of 300 kev (a dose rate of $2.0 \times 10^6$ Gy/hr) and 2.5 Mev (a dose rate of $1.5 \times 10^6$ Gy/hr). Absorbed doses were 5 kGy and 25 kGy at a relative depth of 80% from the surface (current flow: 10.8, 32.1 mA; rate: 50 m/min; irradiation range: 20 cm). The absorbed dose was confirmed by using a cellulose triacetate dosemeter.

A. Measurement of Molecular Weight Distribution

Electron beam-irradiated samples of 10 mg were weighed accurately and water was added to 100 ml in total. The sample solutions were measured by HPLC under the following conditions.
Apparatus: Galliver (Jasco); detector: UV970 (wavelength of 220 nm), columns: TSK guard column SB-G (6 mm×40 mm) and TSK gel G2000SWXL (7.8 mm×300 mm); mobile phase: 50 mM phosphate buffer containing 0.3 M NaCl (pH 7.0); flow rate: 1.0 ml/min; temperature: 40° C.; injection amount: 20 µl.

The obtained results showed a tendency for the thaumatin content to linearly decrease from 100% to 75% in accordance with the increase of the absorbed dose. It was inferred that aromatic amino acids existing on the surface transferred to the inside, changing a state of the amino acid. Any other peaks due to decomposition through the electron beam irradiation were not observed. Peaks due to polymerization were also expected, but it was inferred that thaumatin linkage was weak to such an extent that it disperses into monomolecules due to pressure applied through HPLC and the like.

B. Measurement of Surface Charges

Electron beam-irradiated samples of 10 mg were accurately weighed and water was added to 100 ml in total. The samples were measured by capillary electrophoresis under the conditions described below.
Measurement apparatus: a capillary electrophoresis apparatus G1600 (manufactured by Hewlett-Packard Co.); capillary column: a PVA-coated silica carrier (cell length of 56 cm, inner diameter of 50 µm); buffer: 50 mM phosphate buffer (pH 2.5); injection: pressure-injected at 50 mbar for 30 seconds; voltage: positive voltage of 30 kV, 150 µA at capillary temperature of 20° C.; detection wavelength: 210 nm; band width: 10 nm.

As a result thereof, the surface charges on the protein changed as shown in FIG. 1. In the surface charges, increase of basic residues was observed. At peaks observed during a maintaining time of 8.5 to 11.8 minutes, relative increase of area ratio by about 15% was observed.

C. Static Light Scattering Method

According to a static light scattering method under the following conditions, hydrophilicity on the surface and the molecule size of the irradiated samples were measured.
Measurement apparatus: a static light scattering measurement apparatus DLS-7000HL (manufactured by Otsuka Electronics Co., Ltd.); wavelength: 632.81 nm; average temperature: 25.85° C.; dn/dc: 0.1571 ml/g; refractive index of solvent: 1.3313; angle: 30, 40, 50, 60, 90, 120, 150 (°); solvent: superpure water; filter: 0.1 µm mesh.

As a result thereof, the second virial coefficient changed from $-3.9 \times 10^{-5}$ to $+2.3-2.7 \times 10^{-4}$ (mole·cm$^3$·g$^{-2}$), indicating an increase of hydrophilicity. Through a measurement of the molecular weight, it was observed that the irradiated thaumatin changed to a pentamer or a hexamer (115,000–140,000/22,209), while unirradiated thaumatin is normally a trimer (68,140/22,209) in an aqueous solution (Table 2). Upon calculating an inertia molecule radius which represents fluctuation of particles in water and a particle diameter, the inertia molecule radius of the unirradiated thaumatin was 310 Å whereas that of the irradiated thaumatin was 240 to 270 Å, so that it was inferred that the particle diameter of the obtained associated body was reduced.

TABLE 2

|  | Molecular weight | Second virial coefficient (mole · cm$^3$ · g$^{-2}$) | Inertia molecule radius (Å) |
| --- | --- | --- | --- |
| Unirradiated | 68,140 | $-3.90 \times 10^{-5}$ | 310.8 |
| 2.5 MeV 5 kGy | 114,400 | $2.51 \times 10^{-4}$ | 270.0 |
| 25 kGy | 140,700 | $2.45 \times 10^{-4}$ | 272.5 |
| 300 keV 5 kGy | 116,800 | $2.34 \times 10^{-4}$ | 243.3 |
| 25 kGy | 135,300 | $2.74 \times 10^{-4}$ | 243.6 |

D. Differential Thermal Analysis (DSC)

Dissolving temperatures of the electron beam-irradiated samples and the unirradiated samples were measured under the following conditions.
Measurement apparatus: Micro DSC III (manufactured by SETARAM), weight of sample: 864 mg; protein concentration: 2 wt %; heating rate: 2° K/min, temperature range: 283° K to 373° K (10° C. to 100° C.).

Figure 2:
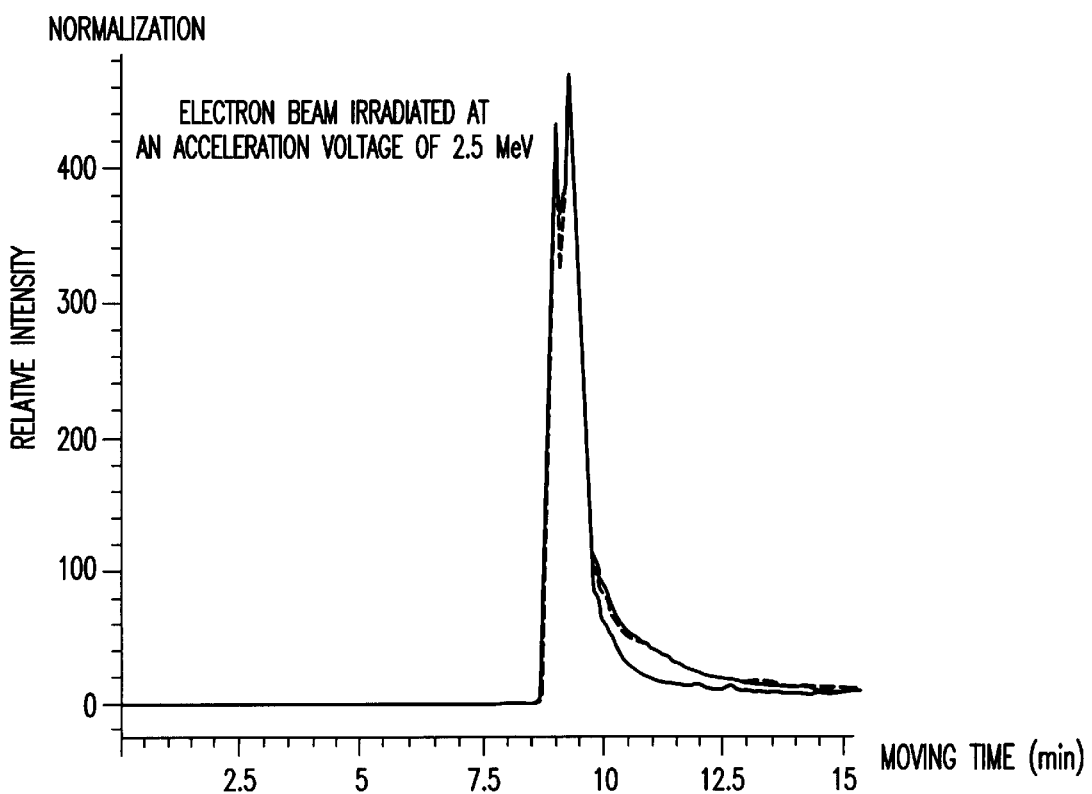
FIG. 2 is a graph illustrating changes in surface charge of thaumatin observed by capillary electrophoresis at an acceleration voltage of 2.5 MeV. A solid line means unirradiated thaumatin, a broken line means thaumatin irradiated at an absorbed dose of 5 kGy and a dotted line means thaumatin irradiated at an absorbed dose of 25 kGy.
Figure 3:
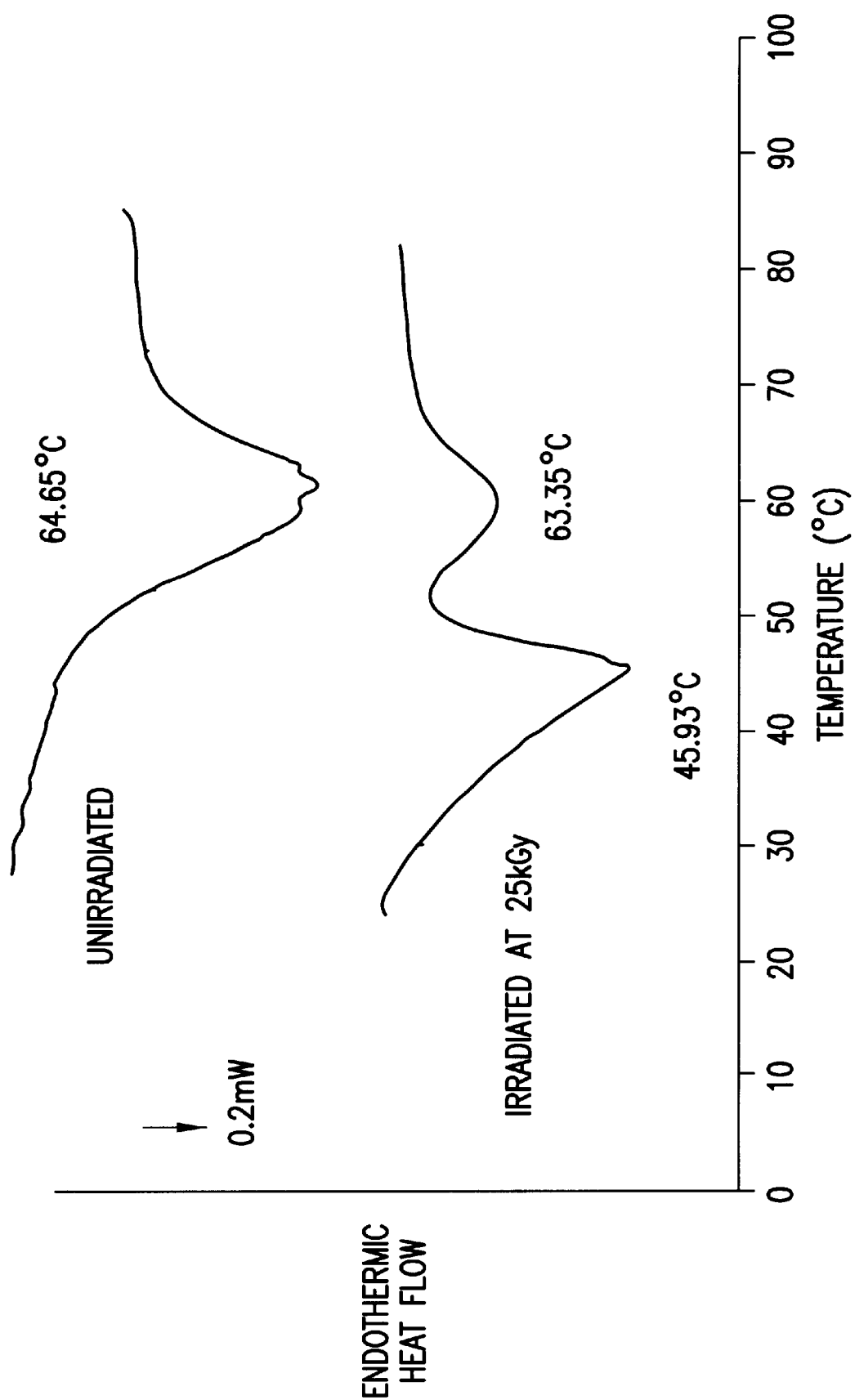
FIG. 3 is a graph illustrating a comparison between unirradiated thaumatin and irradiated thaumatin (25 kGy) by differential thermal analysis.

As shown in FIG. 2, an endothermic peak of the unirradiated thaumatin due to dissolution of hydrophobic colloids in water was observed at about 65° C. In contrast, the irradiated thaumatin showed two peaks considered to be derived from hydrophilic colloids and hydrophobic colloids. The peak derived from the hydrophilic colloids was generated at relatively low temperature (about 45° C.) as compared with the peak derived from the hydrophobic colloids, so that it was found that the irradiated thaumatin can be dissolved uniformly in water at 45° C. or higher. From the results, it was shown that molecules dissolving at lower temperature than usually employed temperature were provided in thaumatin through the electron beam irradiation.

Example 2

Using α-casein (produced by Sigma, Lot No. 82H9575, molecular weight of 23000) as a sample material, electron beam having an absorbed dose of 25 kGy was irradiated at a dose rate of $1.5 \times 10^6$ Gy/hr and an acceleration voltage of 2.5 MeV under the same conditions as in Example 1.

A. Static Light Scattering Method

In the same manner as in Example 1, hydrophilicity on the surface and the molecule size of α-casein irradiated with the electron beam were measured and changes of the molecule were observed.

TABLE 3

| | Molecular weight | Second virial coefficient (mole · cm$^3$ · g$^{-2}$) | Inertia molecule radius (Å) |
|---|---|---|---|
| Unirradiated | $8.13 \times 10^5$ | $-4.38 \times 10^{-5}$ | 884.1 |
| 2.5 MeV 25 kGy | $1.26 \times 10^6$ | $-4.7 \times 10^{-6}$ | 1071.0 |

As a result thereof, hydrophilicity of α-casein also increased through the electron beam irradiation, indicating that water solubility thereof was provided. According to such a characteristic change, a tendency for α-casein to increase from 45 mer to 54 mer was observed. This indicated that the irradiated α-casein increased water solubility and gained stability in an aqueous phase.

B. Differential Thermal Analysis (DSC)

In the same manner as in Example 1, dissolving temperatures of the irradiated α-casein and the unirradiated α-casein were measured.

As a result thereof, the irradiated α-casein of 3 wt % showed a decrease of the dissolving temperature by about 10° C. as compared with the unirradiated α-casein.

Example 3

With a sample material of plasma protein (produced by AMPC, Lot No. F5704) utilized for livestock products by using polyphosphate, electron beam irradiation was performed under the same conditions as in Example 2.

A. Static Light Scattering Method

In the same manner as in Example 1, molecular changes of the irradiated samples and the unirradiated samples were observed and the following results were obtained.

TABLE 4

| | Molecular weight | Second virial coefficient (mole · cm$^3$ · g$^{-2}$) | Inertia molecule radius (Å) |
|---|---|---|---|
| Unirradiated | $2.62 \times 10^8$ | $3.12 \times 10^{-7}$ | 894.9 |
| 2.5 MeV 25 kGy | $3.46 \times 10^8$ | $1.76 \times 10^{-6}$ | 809.5 |

Similar to Examples 1 and 2, hydrophilicity increased through the electron beam irradiation and a tendency for the plasma protein to increase from 6 mer in an ordinary state to 11–12 mer was observed. Thus, it was confirmed that the irradiated plasma protein gained the same properties as those of a protein subjected to solubilization in water, while sufficiently maintaining gelation properties necessary for the plasma protein.

B. Differential Thermal Analysis (DSC)

In the same manner as in Example 1, dissolving temperatures of the irradiated samples and the unirradiated samples were measured.

As a result thereof, the irradiated samples of 3 wt % showed a decrease of the dissolving temperature by about 10° C. as compared with the unirradiated samples.

According to the present invention, provided is a method for improving solubility of a protein in water by irradiating the protein with an electron beam. This method improves the solubility of the protein in water without alteration and decomposition of the protein. Further, an associated body which is not generated in an ordinary state is formed, so that protein which is stable even in an aqueous solution is provided.

What is claimed is:

1. A method for improving solubility of a protein in water comprising irradiating a protein with an electron beam and dissolving the irradiated protein in water.

2. The method according to claim 1, wherein the protein powders or the protein particles are spread thinly in a plastic vessel and the electron beam is irradiated thereon.

3. The method of claim 1, wherein the electron beam is irradiated at an acceleration voltage in the range of 50 KeV to 10 MeV.

4. The method according to claim 3, wherein the range of the acceleration voltage is 300 KeV to 2.5 MeV.

5. The method according to claim 1, wherein the electron beam is irradiated at a dose rate in the range of $1.0 \times 10^5$ to $1.0 \times 10^9$ Gy/hr.

6. The method according to claim 1, wherein a degree of hydrophobicity per amino acid residue constituting the protein is 0.0222 or more.

7. The method according to claim 1, wherein a water content of the protein is 10 wt % or less.

8. The method according to claim 1, wherein the protein is thaumatin, α-casein or plasma protein.

9. The method according to claim 1, wherein the protein is in the form of film, plate, particles or powders.

* * * * *